(12) United States Patent
Belson

(10) Patent No.: US 8,308,754 B2
(45) Date of Patent: Nov. 13, 2012

(54) EMBOLIC PROTECTION DEVICE

(75) Inventor: Amir Belson, Los Altos, CA (US)

(73) Assignee: Emboline, Inc., Los Altos, CA (US)

( * ) Notice: Subject to any disclaimer, the term of this patent is extended or adjusted under 35 U.S.C. 154(b) by 0 days.

(21) Appl. No.: 13/347,046

(22) Filed: Jan. 10, 2012

(65) Prior Publication Data

US 2012/0109183 A1    May 3, 2012

Related U.S. Application Data

(63) Continuation of application No. 10/493,854, filed as application No. PCT/US03/26938 on Aug. 27, 2003, now Pat. No. 8,114,114.

(60) Provisional application No. 60/406,492, filed on Aug. 27, 2002.

(51) Int. Cl.
*A61M 29/00* (2006.01)

(52) U.S. Cl. ................................... 606/200

(58) Field of Classification Search ............ 606/151, 606/157, 200, 213; 623/1.11
See application file for complete search history.

(56) References Cited

U.S. PATENT DOCUMENTS

| | | | |
|---|---|---|---|
| 4,723,549 A | 2/1988 | Wholey et al. | |
| 4,790,809 A | 12/1988 | Kuntz | |
| 5,108,419 A | 4/1992 | Reger et al. | |
| 5,769,816 A | 6/1998 | Barbut et al. | |
| 5,800,525 A | 9/1998 | Bachinski et al. | |
| 6,117,154 A | 9/2000 | Barbut et al. | |
| 6,139,517 A | 10/2000 | Macoviak et al. | |
| 6,254,563 B1 | 7/2001 | Macoviak et al. | |
| 6,348,063 B1 | 2/2002 | Yassour et al. | |
| 6,361,545 B1 | 3/2002 | Macoviak et al. | |
| 6,371,935 B1 | 4/2002 | Macoviak et al. | |
| 6,461,370 B1 | 10/2002 | Gray et al. | |
| 6,499,487 B1 | 12/2002 | McKenzie et al. | |
| 6,537,297 B2 | 3/2003 | Tsugita et al. | |
| 6,695,864 B2 | 2/2004 | Macoviak et al. | |
| 6,746,469 B2 | 6/2004 | Mouw | |
| 6,808,520 B1 | 10/2004 | Fourkas et al. | |
| 7,232,453 B2 | 6/2007 | Shimon | |
| 7,758,606 B2 | 7/2010 | Streeter et al. | |
| 2002/0058964 A1 | 5/2002 | Addis | |

(Continued)

FOREIGN PATENT DOCUMENTS

WO     WO 2004/019817 A1     3/2004

OTHER PUBLICATIONS

Office action dated Jan. 17, 2012 for U.S. Appl. No. 12/532,630.

(Continued)

*Primary Examiner* — Corrine M McDermott
*Assistant Examiner* — Gregory Anderson
(74) *Attorney, Agent, or Firm* — Wilson, Sonsini, Goodrich & Rosati

(57) ABSTRACT

The embolic protection device (10) has an expandable tubular structure supporting a filter mesh material (12). The embolic protection device is compressed to a small diameter for insertion into a patient's aorta, then expanded within the aorta with the filter mesh material positioned to allow blood to enter sidebranch vessels connected to the aorta and to prevent embolic material from entering the sidebranch vessels. The filter mesh material may be configured with waves or undulations (26) for increased surface area and/or with two layers of mesh material to provide additional protection against embolization and to prevent inadvertent occlusion of the sidebranch vessels.

14 Claims, 5 Drawing Sheets

U.S. PATENT DOCUMENTS

| | | |
|---|---|---|
| 2003/0040736 A1 | 2/2003 | Stevens et al. |
| 2003/0100940 A1 | 5/2003 | Yodfat |
| 2004/0034380 A1 | 2/2004 | Woolfson et al. |
| 2004/0073253 A1 | 4/2004 | Morrill et al. |
| 2004/0215167 A1 | 10/2004 | Belson |
| 2004/0225354 A1 | 11/2004 | Allen et al. |
| 2005/0010246 A1 | 1/2005 | Streeter et al. |
| 2010/0312268 A1 | 12/2010 | Belson |

OTHER PUBLICATIONS

U.S. Appl. No. 13/343,538, filed Jan. 4, 2012, Belson.

US 6,348,062, 02/2002, Hopkins et al. (withdrawn).

International search report dated Jan. 15, 2004 for PCT/US2003/026938.

International search report and written opinion dated Apr. 9, 2008 for PCT/US2007/024558.

EMBOLIC PROTECTION DEVICE

CROSS-REFERENCE TO RELATED APPLICATION

This application is a continuation of U.S. patent application Ser. No. 10/493,854, filed Apr. 27, 2004, which is a National Stage Application of PCT/US2003/26938, filed Aug. 27, 2003, which claims the benefit of U.S. Provisional Application No. 60/406,492, filed Aug. 27, 2002, the full disclosures of which are incorporated herein by reference.

BACKGROUND OF THE INVENTION

Field of the Invention

The present invention relates to apparatus and methods for providing embolic protection to a patient's aortic arch vessels during cardiac surgery and interventional cardiology procedures.

Cerebral embolism is a known complication of cardiac surgery, cardiopulmonary bypass and catheter-based interventional cardiology and electrophysiology procedures. Embolic particles, which may include thrombus, atheroma and lipids, may become dislodged by surgical or catheter manipulations and enter the bloodstream, embolizing in the brain or other vital organs downstream. Cerebral embolism can lead to neuropsychological deficits, stroke and even death. Prevention of cerebral embolism would benefit patients and improve the outcome of these procedures.

Previous devices for preventing cerebral embolism are described in the following U.S. patents and patent applications, which are hereby incorporated by reference: U.S. Pat. No. 6,371,935 Aortic catheter with flow divider and methods for preventing cerebral embolization, U.S. Pat. No. 6,361,545 Perfusion filter catheter, U.S. Pat. No. 6,254,563 Perfusion shunt apparatus and method, U.S. Pat. No. 6,139,517 Perfusion shunt apparatus and method, U.S. Pat. No. 6,537,297 Methods of protecting a patient from embolization during surgery, U.S. Pat. No. 6,499,487 Implantable cerebral protection device and methods of use, U.S. Pat. No. 5,769,816 Cannula with associated filter, US20030100940A1 Implantable intraluminal protector device and method of using same for stabilizing atheromas.

BRIEF SUMMARY OF THE INVENTION

The present invention takes the form of apparatus and methods for providing embolic protection to a patient's aortic arch vessels during cardiac surgery and interventional cardiology and electrophysiology procedures. Embolic particles in the aortic blood flow are prevented from entering the aortic arch vessels and carotid arteries that lead to the brain. The apparatus and methods of the present invention can also be used for embolic protection of other organ systems, such as the renal system.

In one embodiment, a stent-like embolic protection device is constructed of a self-expanding tubular mesh that may be woven out of wires or fibers or formed from a tube or sheet. The embolic protection device is compressed to a small diameter and inserted into a delivery tube or catheter, which is introduced via a peripheral artery or an aortotomy and advanced into the aortic arch. Once in place, the delivery tube is withdrawn to allow the device to expand similar to a self-expanding stent. The mesh of the device covers the ostia of the arch vessels, allowing blood to enter, but preventing potential emboli from entering the aortic arch vessels and carotid arteries. The device conforms closely to the walls of the aorta so that it will not interfere with performing cardiac surgery or interventional cardiology procedures. The embolic protection device may be collapsed and withdrawn from the aorta after the procedure or it may be left in the aorta for long-term embolic protection.

In another embodiment, the embolic protection device may be made with a flat panel of fine mesh textile fabric that is supported on a wire frame or the like. The panel of fine mesh fabric is held in place over the aortic arch vessels by the wire frame to filter out potential emboli. Being made of fabric, the device is free to conform to the ostia of the arch vessels to allow more surface area for blood flow compared to a flat panel. The wire frame may be attached to a handle or cannula for insertion through an aortotomy or to a catheter for peripheral artery insertion. In addition, the wire frame may include one or more wire hoops or a stent-like tubular structure for supporting the embolic protection device within the aortic arch.

Additional features are described which may be used with either embodiment of the embolic protection device. An embolic protection device is described with waves or undulations to provide more surface area for filtering out potential emboli and to prevent inadvertent occlusion of the arch vessels. Another embolic protection device is described with two layers of mesh material to provide additional protection against embolization and to prevent inadvertent occlusion of the arch vessels. An embolic protection device is described with an inflatable toroidal balloon for supporting the filter mesh material within the aorta. The embolic protection device or a portion of it may be coated with an antithrombogenic coating to reduce the formation of clots that could become potential emboli.

DETAILED DESCRIPTION OF THE INVENTION

Figure 1:
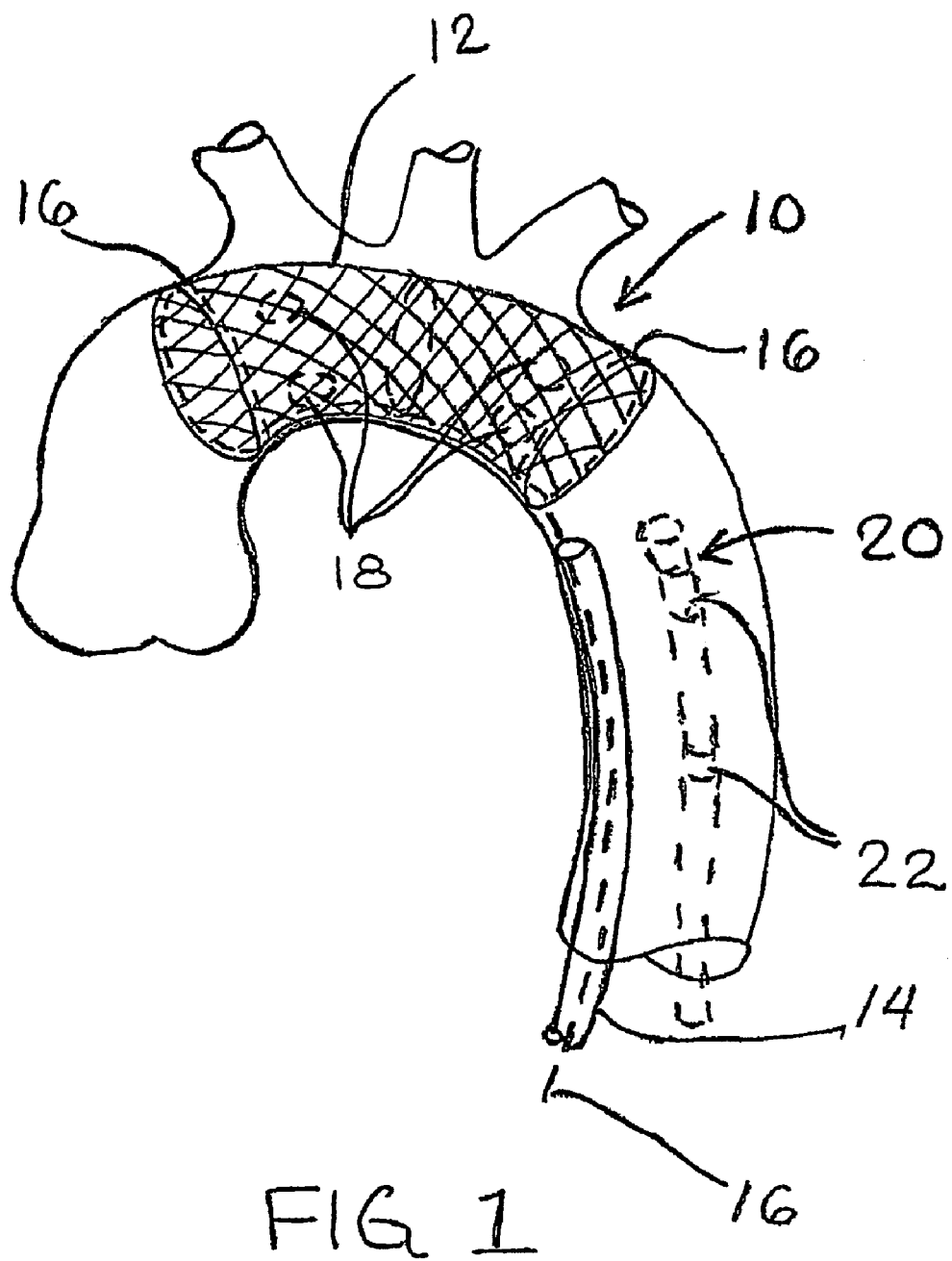
FIG. 1 shows a stent-like embolic protection device deployed within a patient's aortic arch for protecting the aortic arch vessels and carotid arteries from potential emboli.

FIG. 1 shows a stent-like embolic protection device 10 deployed within a patient's aortic arch for protecting the aortic arch vessels and carotid arteries from potential emboli. The embolic protection device 10 is made of a resilient material, either a polymer or a metal (e.g. Nitinol) or a combination of materials. The device 10 may be woven out of wires or fibers to form a tubular mesh structure 12 or by slitting and expanding a tube or sheet. Alternatively, the device 10 may be constructed with a tubular mesh structure 12 made of a flexible textile mesh with one or more wire hoops or a stent-like tubular structure for supporting the tubular mesh structure 12 within the aortic arch. The device 10 is compressible to a small diameter for insertion into the aorta via peripheral artery access or through an aortotomy. The device 10 is preferably self-expanding and, when expanded, has a generally tubular shape that conforms to the diameter and curvature of the aortic arch.

The embolic protection device 10 is compressed to a small diameter and inserted into a delivery tube or catheter 14. The delivery tube is introduced via a peripheral artery or an aortotomy and advanced into the aortic arch. Once in place, the delivery tube 14 is withdrawn to allow the device 10 to expand similar to a self-expanding stent. The mesh 12 of the device covers the ostia of the arch vessels, allowing blood to enter, but preventing potential emboli from entering the aortic arch vessels and carotid arteries. The device 10 conforms closely to the walls of the aorta so that it will not interfere with performing cardiac surgery or catheter-based interventional cardiology or electrophysiology procedures.

Alternatively, the embolic protection device 10 may be balloon-expandable. In this case, the embolic protection device 10 would be crimped or compressed onto an expandable balloon mounted on a catheter. The catheter is introduced into the aortic arch and the balloon is expanded to deploy the embolic protection device 10 in the aorta. Other volume expanding mechanisms, such as a mechanical expander, may be used in lieu of an expandable balloon.

After the procedure is completed, the embolic protection device 10 may be compressed and withdrawn from the aorta. Alternatively, the device 10 may be left in the aorta for long-term embolic protection. The device 10 may be compressed using one or more drawstrings 16 that encircle the device. The drawstrings 16 are pulled to compress the device and the device is withdrawn into the delivery tube 14 for removal. Alternatively, the embolic protection device 10 may be stretched longitudinal with the aid of a catheter, which will cause the diameter of the device to contract. Alternatively, the embolic protection device 10 may use a magnetic mechanism for compressing the device for removal. Multiple magnets 18 are arranged around the periphery of the device 10. After the procedure is completed, a catheter 20 carrying one or more strong magnets 22 is inserted through the lumen of the device 10 to compress the device around the catheter for removal.

Figure 2:
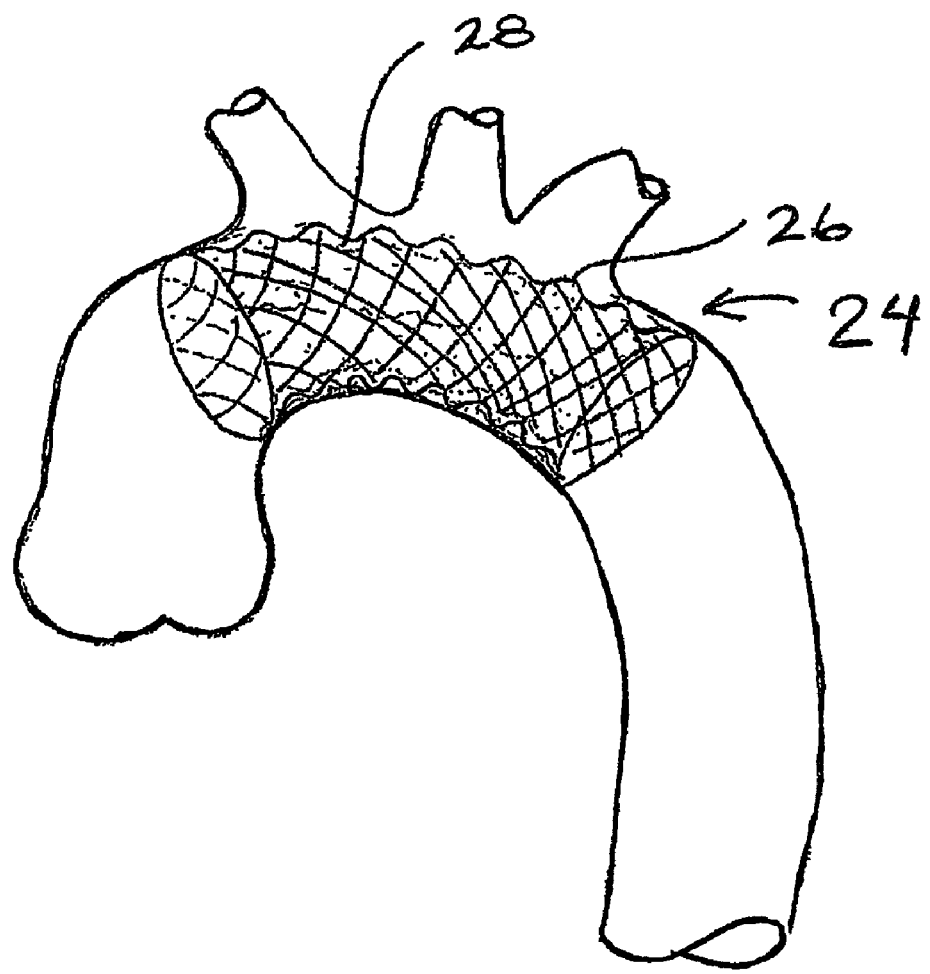
FIG. 2 shows a stent-like embolic protection device with waves or undulations.

FIG. 2 shows a stent-like embolic protection device 24 with waves or undulations 26 in the tubular mesh structure 28. The waves or undulations 26 in the embolic protection device 24 provide more surface area for filtering out potential emboli and prevents inadvertent occlusion of the arch vessels. This feature may be combined with any of the other embodiments and features of the invention described herein.

Figure 3:
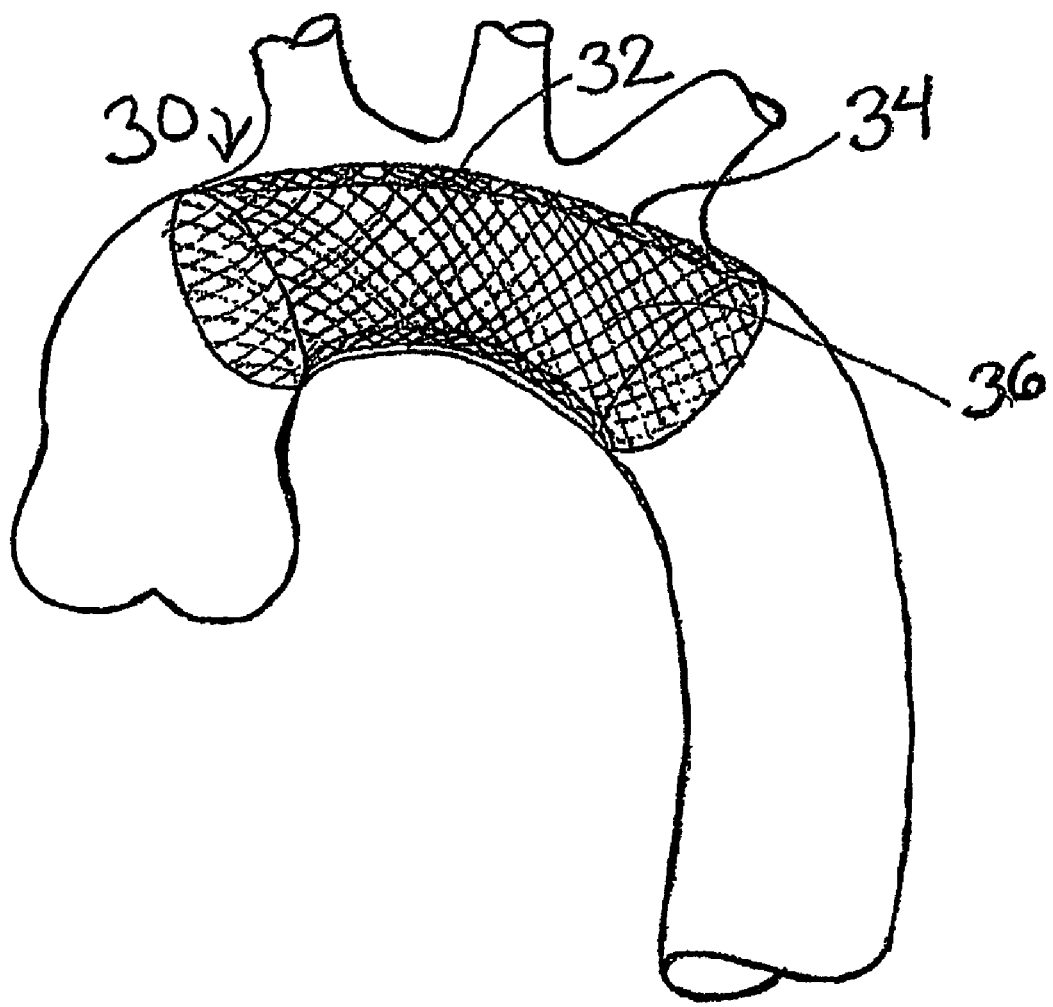
FIG. 3 shows a cut-away view of a stent-like embolic protection device with two layers of mesh material.

FIG. 3 shows a cut-away view of a stent-like embolic protection device 30 wherein the tubular mesh structure 32 is constructed with two layers of mesh material. The embolic protection device 30 preferably has an outer layer 34 of fine mesh material and an inner layer 36 of coarse mesh material. The outer layer 34 is shown cut away so that the inner layer 36 is visible. One or both layers of the device 30 may be self-expanding. For example, the outer layer 34 may be made of a fine mesh textile fabric, while the inner layer 36 is made with a self-expanding wire mesh structure. The two-layer structure provides additional protection against embolization and prevents the fine mesh of the outer layer 34 from becoming clogged with large emboli. Also, because blood can flow between the inner and outer layers of the device, all of the arch vessels will continue to receive blood flow even if the inner layer in front of one or more of the vessels becomes clogged. This feature may be combined with any of the other embodiments and features of the invention described herein. For example, one or both layers of the two-layer construction may be made with waves or undulations as described above in connection with FIG. 2.

Figure 4:
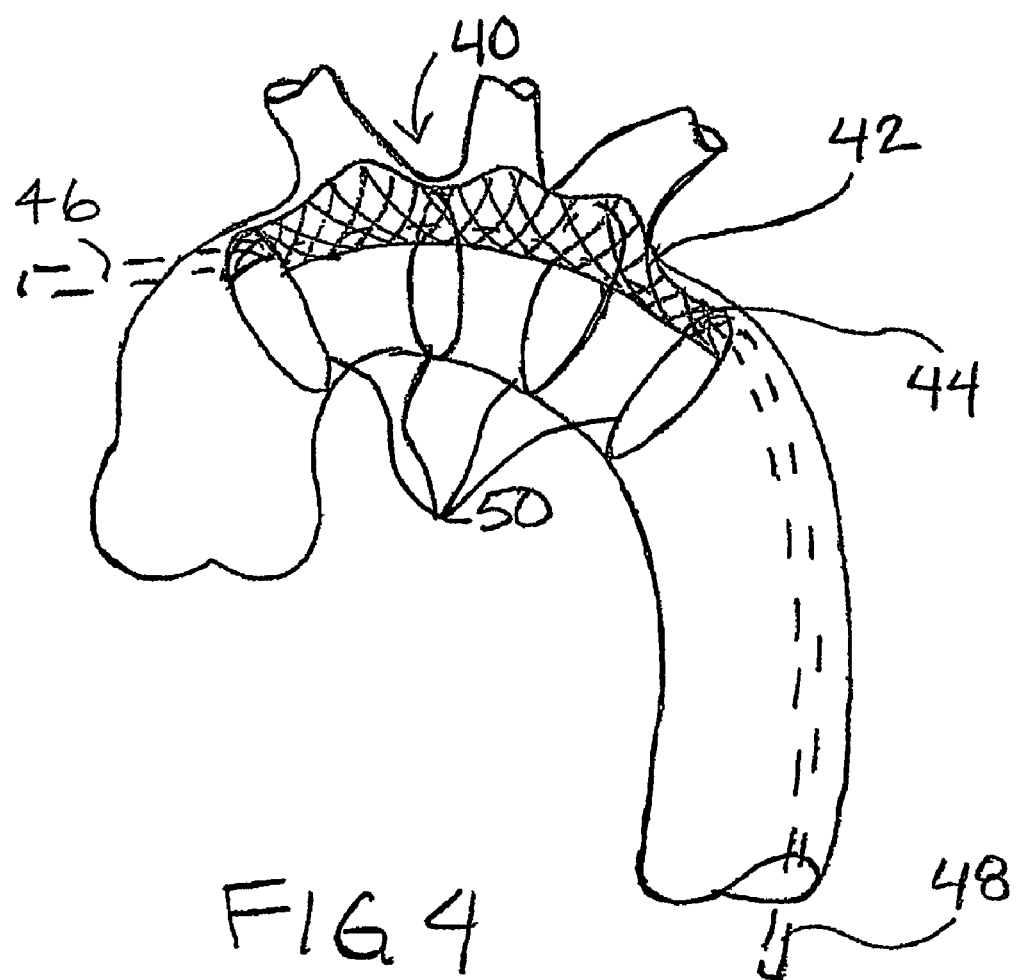
FIG. 4 shows an alternative embodiment of an embolic protection device.

FIG. 4 shows an alternative embodiment of an embolic protection device 40. In this embodiment, the embolic protection device 40 may be made with a panel of fine mesh textile fabric 42 that is supported on a wire frame 44 or the like. The panel of fine mesh fabric 42 is held in place over the aortic arch vessels by the wire frame 44 to filter out potential emboli. Being made of fabric, the mesh panel 42 is free to conform to the ostia of the arch vessels to allow more surface area for blood flow compared to a totally flat panel.

The wire frame 44 may be attached to a handle or cannula 46 for insertion through an aortotomy or to a catheter 48 for peripheral artery insertion. Alternatively or in addition, the wire frame 44 may include one or more wire hoops 50 or a stent-like tubular structure for supporting the embolic protection device 40 within the aortic arch. This embodiment and/or its features may be combined with any of the other embodiments and features of the invention described herein. For example, the mesh panel 42 may be made with waves or undulations as described above in connection with FIG. 2 and/or with a two-layer construction as described in connection with FIG. 3. As a further example, the handle, cannula 46 or catheter 48 for insertion of the embolic protection device 40 described in connection with FIG. 4 may also be combined with any of the embolic protection devices described in connection with FIGS. 1-3 and 5.

Figure 5:
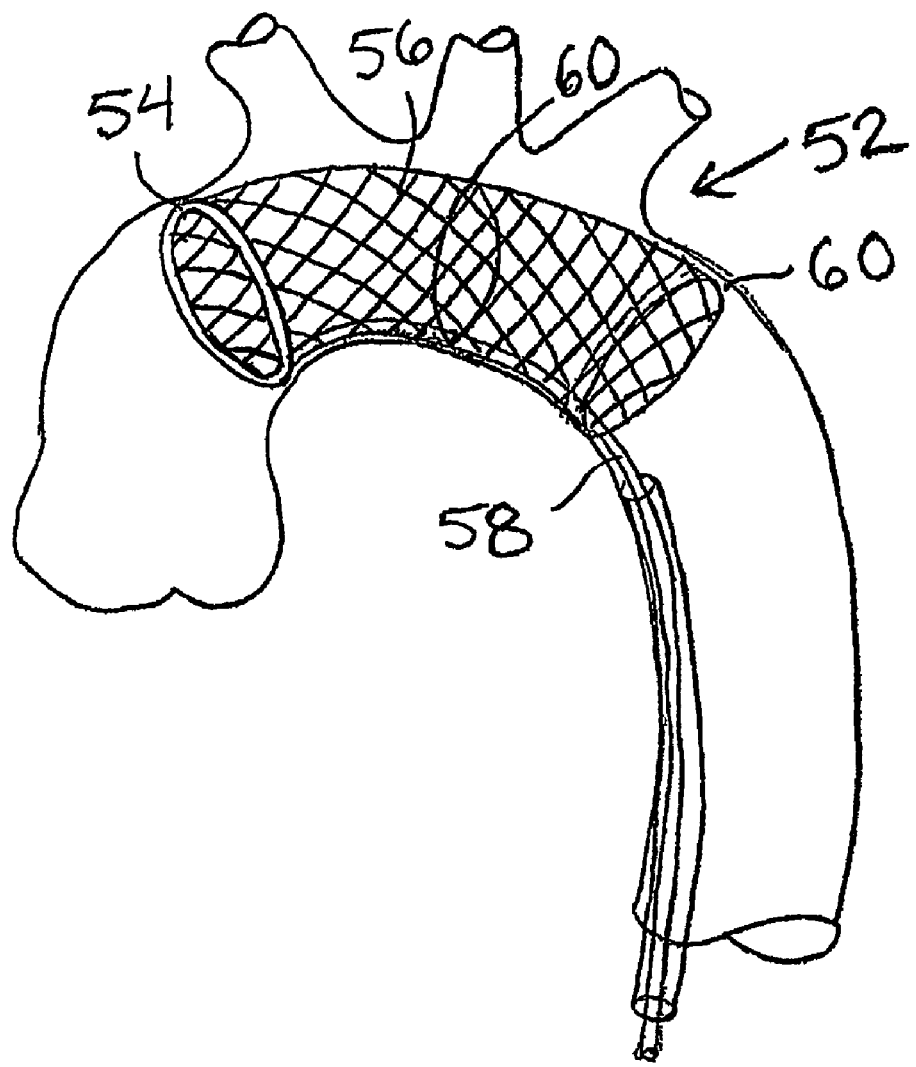
FIG. 5 shows another alternative embodiment of an embolic protection device.

FIG. 5 shows another alternative embodiment of an embolic protection device 52. An inflatable toroidal balloon 54 supports the upstream end of a tubular mesh structure 56. The toroidal balloon 54 is inflated and deflated through a catheter 58 having an inflation lumen and, optionally, a guidewire lumen. The tubular mesh structure 56 may be a self-expanding structure woven of wires or fibers or it may be a flexible textile mesh. Optionally, one or more wire hoops 60 or the like may be used to support the tubular mesh structure 56 within the patent's aorta. Alternatively, one or more additional inflatable toroidal balloons 54 may be used in place of the optional wire hoops 60 to support the tubular mesh structure 56. The features of this embodiment may be combined with any of the other embodiments and features of the invention described herein. For example, one or more inflatable toroidal balloons 54 may be combined with the embolic protection devices described in connection with FIGS. 1-3 for supporting a tubular mesh structure or panel of mesh material.

The entire embolic protection device or a portion of it may be coated with an antithrombogenic coating, for example a bonded heparin coating, to reduce the formation of clots that could become potential emboli. Alternatively or in addition, the embolic protection device or a portion of it may have a drug-eluting coating containing an anti-inflammatory or anti-stenosis agent.

The embolic protection device of the present invention can also be used for embolic protection of other organ systems. For example, an embolic protection device can be deployed in the patient's descending aorta for preventing embolic particles in the aortic blood flow from entering the renal arteries and embolizing in the patient's kidneys.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:
1. An embolic protection device for deployment within a patient's aorta comprising:
 a substantially flat panel of filter mesh material supported on a wire frame, the wire frame surrounding a periphery of the substantially flat panel of filter mesh material, and at least one structure connected to the wire frame configured for engaging an interior wall of the aorta to support the embolic protection device within the patient's aorta, the embolic protection device having a compressed position, wherein the embolic protection device is compressed to a small diameter for insertion into the patient's aorta, and an expanded position, wherein the embolic protection device expands to a larger size within the patient's aorta, wherein, when the embolic protection device is in the expanded position, the at least one structure expands away from a plane of the flat panel of filter mesh material to a deployed position configured to support the wire frame and the panel of filter mesh material within the aorta such that the filter mesh material conforms to ostia of sidebranch vessels connected to the patient's aorta and allows blood to enter the sidebranch vessels, but prevents embolic material from entering the sidebranch vessels, and wherein a portion of the at least one structure extending away from the flat panel of filter mesh material is not covered by or directly attached to the filter mesh material.

2. The embolic protection device of claim 1, wherein the support comprises at least one wire hoop connected to the wire frame, extending away from the plane of the flat panel of filter mesh material and supporting the embolic protection device within the patient's aorta when the embolic protection device is in the expanded position.

3. The embolic protection device of claim 1, wherein the wire frame supporting the panel of filter mesh material is a self-expanding structure.

4. The embolic protection device of claim 1, wherein the filter mesh material is configured with waves or undulations.

5. The embolic protection device of claim 1, wherein the panel of filter mesh material is configured with a first layer constructed of a fine mesh textile fabric and a second layer constructed of a self-expanding wire mesh structure.

6. The embolic protection device of claim 1, wherein the panel of filter mesh material is configured with a first layer of a coarse mesh material and a second layer of a fine mesh material.

7. The embolic protection device of claim 1, further comprising a delivery tube sized and configured to hold the embolic protection device in its compressed position.

8. The embolic protection device of claim 1, further comprising a drawstring encircling the tubular structure for selectively compressing the tubular structure to a small diameter for withdrawal from the patient.

9. A method of providing embolic protection for sidebranch vessels connected to a patient's aorta comprising:

introducing an embolic protection device into the patient's aorta, the embolic protection device comprising a wire frame supporting a substantially flat panel of filter mesh material, the wire frame surrounding a periphery of the substantially flat panel of filter mesh material, and at least one structure connected to the wire frame configured for engaging an interior wall of the aorta to support the embolic protection device within the patient's aorta, the embolic protection device having a compressed position, wherein the embolic protection device is compressed to a small diameter for insertion into the patient's aorta; and expanding the embolic protection device to an expanded position within the patient's aorta, wherein, when the embolic protection device is in the expanded position, the at least one structure expands away from a plane of the flat panel of filter mesh material to a deployed position configured to support the wire frame and the panel of filter mesh material within the aorta such that the filter mesh material conforms to ostia of the sidebranch vessels from the patient's aorta and allows blood to enter the sidebranch vessels, but prevents embolic material from entering the sidebranch vessels, wherein a portion of the at least one structure extending away from the flat panel of filter mesh material is not covered by or directly attached to the filter mesh material.

10. The method of claim 9, wherein the filter mesh material is configured with waves or undulations.

11. The method of claim 9, wherein the panel of filter mesh material is configured with a first layer constructed of a fine mesh textile fabric and a second layer constructed of a self-expanding wire mesh structure.

12. The method of claim 9, wherein the panel of filter mesh material is configured with a first layer of a coarse mesh material and a second layer of a fine mesh material.

13. The method of claim 9, further comprising compressing the embolic protection device into a delivery tube for introduction of the embolic protection device into the aorta.

14. The method of claim 9, wherein the method further comprises drawing a drawstring encircling the tubular structure to compress the tubular structure to a small diameter prior to withdrawal from the patient.

\* \* \* \* \*